United States Patent [19]
Kopp-Holtwiesche et al.

[11] Patent Number: 5,635,392
[45] Date of Patent: Jun. 3, 1997

[54] NUTRIENT MIXTURES FOR THE BIOREMEDIATION OF POLLUTED SOILS AND WATERS

[75] Inventors: Bettina Kopp-Holtwiesche, Duesseldorf; Albrecht Weiss, Langenfeld; Adelheid Boehme, Duesseldorf, all of Germany

[73] Assignee: Henkel Kommanditgesellschaft auf Aktien, Duesseldorf, Germany

[21] Appl. No.: 347,351

[22] PCT Filed: May 26, 1993

[86] PCT No.: PCT/EP93/01323

§ 371 Date: Dec. 1, 1994

§ 102(e) Date: Dec. 1, 1994

[87] PCT Pub. No.: WO93/24612

PCT Pub. Date: Dec. 9, 1993

[30] Foreign Application Priority Data

Jun. 3, 1992 [DE] Germany .................. 42 18 243.3

[51] Int. Cl.⁶ .......................... C02F 3/00; C12N 1/20
[52] U.S. Cl. .......................... 435/253.6; 210/604
[58] Field of Search .................. 210/604; 435/253.6

[56] References Cited

U.S. PATENT DOCUMENTS

| | | | |
|---|---|---|---|
| 4,276,094 | 6/1981 | Gutnick et al. | 134/10 |
| 4,462,910 | 7/1984 | Lepain et al. | 210/610 |
| 5,106,516 | 4/1992 | Mueller et al. | 507/138 |
| 5,232,910 | 8/1993 | Mueller et al. | 507/138 |
| 5,252,554 | 10/1993 | Mueller et al. | 507/138 |
| 5,254,531 | 10/1993 | Mueller et al. | 507/131 |
| 5,318,954 | 6/1994 | Mueller et al. | 507/138 |
| 5,318,955 | 6/1994 | Mueller et al. | 507/139 |

FOREIGN PATENT DOCUMENTS

| | | |
|---|---|---|
| 2739428 | 3/1978 | Germany . |
| 3842659 | 6/1990 | Germany . |
| 3842703 | 6/1990 | Germany . |
| 3903784 | 8/1990 | Germany . |
| 3903785 | 8/1990 | Germany . |
| 3907391 | 9/1990 | Germany . |
| 3907392 | 9/1990 | Germany . |
| 3911238 | 10/1990 | Germany . |
| 3911299 | 10/1990 | Germany . |
| 4018228 | 12/1991 | Germany . |
| 4131714 | 5/1993 | Germany . |
| 2065631 | 7/1981 | United Kingdom . |
| 2115399 | 9/1983 | United Kingdom . |

OTHER PUBLICATIONS

Water Environment Research vol. 64, No. 2, Apr. 1992, Alexandria, VA, pp. 163–169, D.M. Falatko et al "Effects of Biologically Produced Surfactants on the Mobility and Biodegradatin of Petroleum Hydrocarbons" see page 167, column 2 –page 168.

Chemische Industrie May 1991, 10 to 12 "Hunger for Crude Oil".

Erdöl und Kohle –Erdgas, 44, Apr. 1991, 197 to 200, Th. Höpner et al. "Die Ölkatastrophe im Persisch–Arabischen Golf".

"Bioremediation of Hazardous Waste" in Biofuture, Sep. 1990, 24 to 35.

*Primary Examiner*—Michael G. Wityshyn
*Assistant Examiner*—Deborah Ware
*Attorney, Agent, or Firm*—Ernest G. Szoke; Wayne C. Jaeschke; Henry E. Millson, Jr.

[57] ABSTRACT

A nutrient concentrate for stimulation of growth for the accelerated cultivation and growth of hydrocarbon-consuming microorganisms as well as a process for their use in bioremediation is disclosed. The concentrate is an admixture of water-soluble and/or oil-soluble compounds of phosphorus (P) and nitrogen (N) and other components. The concentrate is in the form of a liquid water-based preparation and contains an ester of phosphoric acid as both an emulsifier and a P source. Further, from 10 to 40% by weight urea is contained in the concentrate as a N source. The invention also relates to the treatment of polluted soils, waters, and articles using a diluted aqueous solution of the concentrated admixture.

20 Claims, No Drawings

NUTRIENT MIXTURES FOR THE BIOREMEDIATION OF POLLUTED SOILS AND WATERS

BACKGROUND OF THE INVENTION

Controlling pollution caused by hydrocarbon compounds, for example crude oil pollution, in soils and waters by bioremediation is acquiring increasing significance. Major advantages are afforded by the inexpensive in situ processes where no space is required for waste disposal. Microorganisms which consume hydrocarbon compounds are valuable tools in the context of this technology, even under comparatively unfavorable basic conditions, providing their enrichment and/or their growth at the point of pollution can be sufficiently stimulated. From the more recent literature, reference is made to the articles in Chemische Industrie 5/91, 10 to 12 "Hunger for Crude Oil" and in Erdöl und Kohle-Erdgas, 44, April 1991, 197 to 200, Th. Höpner et al. "Die Ölkatastrophe im Persisch-Arabischen Golf (The Oil Catastrophe in the Persian/Arabian Gulf)" and the extensive literature cited therein.

The working principle of bioremediation is based on optimal promotion of the growth of the pollution-consuming microorganism populations. Two important aids are of paramount significance in this regard: firstly, the supply of growth-promoting elements which are generally not available in sufficient concentrations in the polluted area. These growth-promoting elements are primarily inorganic and/or organic compounds of nitrogen and phosphorus which are made available as nutrient concentrates for stimulation and as growth aids for the accelerated growth of the microorganisms consuming hydrocarbon compounds. Secondly, preformed concentrates of suitable hydrocarbon-consuming microorganisms are frequently used, in particular to accelerate biological degradation in the initial phases, and may be applied to the polluted areas, for example at weekly intervals. However, depending on the particular situation, more particularly the previous individual history of the polluted areas to be treated, it may even be assumed that the use of microorganism concentrates is not necessary. In general, this will always be the case when the natural process of biological degradation has already resulted in the development of sufficient concentrations of microorganism strains, cf. in this connection for example the 2nd of the literature references cited at the beginning.

Hitherto unpublished German patent application DE-P 41 31 714.9 proposes an improved nutrient mixture for the bioremediation of polluted soils and waters. The mixture described in this document is in the form of a storable solution or emulsion and contains P- and N-sources in a liquid mixed phase of biocompatible water-soluble carrier components based on glycerol and biocompatible oil-soluble carrier components based on glycerol esters. Although the application in question proposes a solution in which only substances which are readily biodegradable are introduced into the contaminated soil sample, another C-source is introduced on a significant scale in the form of the glycerol esters. Under unfavorable growth conditions, the presence of these components can promote the growth of microorganisms which are unsuitable for degrading pollutants so that they proliferate to the detriment of the degrading microorganisms.

DESCRIPTION OF THE INVENTION

Against this background, the problem addressed by the present invention was to provide a nutrient mixture which would have an emulsifying effect and which would contain P- and N-yielding substances, but would be made up of very few pure C-compounds.

Another problem addressed by the invention was to prepare this nutrient mixture in such a way that it would leave very few residues behind in the soil sample to be treated. A further problem addressed by the invention was to provide a nutrient mixture which would prefer the pollutant degrading microorganisms to other microorganisms.

In a first embodiment, therefore, the present invention relates to a nutrient concentrate for stimulation and as a growth aid for the accelerated growth of hydrocarbon-consuming microorganisms for their use in the biological degradation of organic components, containing water-soluble and/or oil-soluble compounds of phosphorus (P) and nitrogen (N) present in admixture with other water-soluble and/or oil-soluble organic mixture components which are at least partly endowed with nutrient character for the growth of the microorganisms, characterized in that it is in the form of a liquid water-based preparation and contains one or more esters of phosphoric acid as emulsifier and P-source and, if desired, one or more water-soluble or water-dispersible N-sources.

The present invention also relates to the use of the nutrient mixtures in combination with concentrates of microorganisms which are capable of degrading hydrocarbon compounds and which are preferably of natural origin. Important applications include the remediation of soils, fresh water and/or salt water through the elimination of pollution based on hydrocarbon compounds and also the treatment of working equipment, pipes, large vessels, including tankers and the like, using the nutrient mixtures according to the invention.

In one particular embodiment, the invention relates to the use of the nutrient mixtures, more particularly in combination with microorganism concentrates capable of degrading hydrocarbon compounds, for the elimination of oil-wetted cuttings from geological land-supported or offshore drilling, for example from the development of geological occurrences.

In the context of the invention, particular significance is attributed to the phosphoric acid esters used. These compounds act on the one hand as a P-source and on the other hand as emulsifiers. Although the way in which they act is not fully understood, it may be assumed that the compounds collect at the interface between the hydrophobic pollutant and the water present in the soil sample and, on the one hand, develop an emulsifying effect and, on the other hand, keep the phosphorus source available in the immediate vicinity of the pollutant, so that it is useful in particular to those microorganisms which are capable of degrading the pollutants. Preferred phosphoric acid esters are those which can be taken up by microorganisms. Accordingly, among the compounds which meet this requirement, particular significance is attributed to the phospholipids. Phospholipids are amphiphilic substances which are obtained from vegetable or animal cells. Preferred phospholipids are the glycerophospholipids which, normally, are also known as lecithin. The sphingophospholipids are less preferred. Known compounds which may be used in accordance with the invention are the diacyl phospholipids, phosphatidyl cholines, phosphatidyl ethanolamines, phosphatidyl inositols, phosphatidyl serines, phosphatidyl glycerols, phosphatidyl glycerol phosphates, diphosphatidyl glycerol, N-acyl phosphatidyl ethanolamine and phosphatidic acid. Preferred compounds are the monoacyl phospholipids, lysophosphatidyl cholines, lysophosphatidyl ethanolamines, lysophosphatidyl inositols, lysophosphatidyl serines, lysophosphatidyl glycerols, lysophosphatidyl glycerophosphates, lysodiphosphatidyl glycerols, lyso-n-acyl phosphatidyl ethanolamines and lysophosphatidic acid. By virtue of their accessibility, the expert will mainly use commercially available phosphatidyl glycerides which are marketed as vegetable or animal lecithins and cephalins. These preparations are generally obtained from oils, such as wheatgerm oil or cottonseed oil or soybean oil. According to the invention, preference is attributed to the enzymatically hydrolyzed glycerophospholipids (enzymatically hydrolyzed lecithin) which are more hydrophilic in character through the elimination of a fatty acid residue. The only exception of those products which have lost their phosphoric acid component as a result of the enzymatic hydrolysis.

In addition to or instead of the phospholipids mentioned above, partial esters of phosphoric acid with fatty alcohols, more particularly corresponding partial esters with linear fatty alcohols, may also be used as the P-source of the nutrient concentrates according to the invention. Esters of relatively short-chain fatty alcohols, i.e. for example $C_{6-10}$ fatty alcohols, are particularly suitable. However, alkylphosphates with relatively long fatty alcohols, i.e. $C_{12-24}$ fatty alcohols, may also be used. Fatty alcohol ether phosphates are also suitable. These are phosphoric acid partial esters of ethoxylated fatty alcohols, the fatty alcohols containing 8 to 24 carbon atoms and being ethoxylated with 1 to 10 moles and preferably 4 to 6 moles of ethylene oxide per mole of fatty alcohol.

The phosphoric acid esters mentioned are used in the nutrient concentrates according to the invention in quantities of 10 to 40% by weight and preferably in quantities of 20 to 30% by weight.

In addition, the nutrient concentrates according to the invention contain an N-source in the form of inorganically and/or organically bound nitrogen. N-sources which only contain organically bound nitrogen are preferred because the use of inorganically bound nitrogen can result in salinization of the soil.

Suitable N-sources of the type in question are, for example, inorganic salts, such as alkali metal nitrate or nitrites, or ammonium salts, for example ammonium sulfate or, in particular, ammonium nitrate. Organic N-sources are biocompatible organic nitrogen compounds. In the context of the teaching according to the invention, urea has proved to be particularly accessible for controlling and promoting microorganism growth and may be present in the nutrient concentrates in quantities of around 10 to 40% by weight and, more particularly, in quantities of 15 to 30% by weight. It has been found in this regard that, where urea is used in the above-mentioned concentrations, it has a preserving effect against unwanted microbial contamination so that the nutrient concentrates have the high stability required for storage.

In one particular embodiment of the invention, the nutrient mixtures according to the invention may be used without an additional N-source where phospholipids are used as the P-source because phospholipids contain both P and N.

To support the emulsifying effect of the phosphoric acid esters, the nutrient concentrates according to the invention may contain biocompatible surfactants (except for the glycerol esters claimed in earlier application DE 41 31 714). Anionic surfactants, mixtures of anionic and nonionic surfactants and nonionic surfactants alone may be used for this purpose. Suitable anionic surfactants are readily biodegradable anionic surfactants, such as soaps for example.

Alkylsulfates, more particularly fatty alcohol sulfates, may also be used. Anionic surfactants based on petrochemicals, such as alkylbenzenesulfonate or alkylethersulfates, for example, are less suitable. Preferred nonionic surfactants are alkyl glycoside compounds which have preferably been obtained from straight-chain fatty alcohols containing at least 8 carbon atoms. Suitable alkyl glycoside compounds contain, for example, $C_{8-18}$ and, more particularly, $C_{10-18}$ fatty alcohol components and have an average degree of polymerization of the oligoglycosides of around 1.2 to 5. Corresponding alkyl glycoside compounds with a DP value of around 1.5 to 5 may be regarded not only as effective surface-active additives of the o/w type, particularly where they have HLB values of around 10 to 18, they are also distinguished by particular biocompatibility which is attributable inter alia to their comparatively rapid degradability.

However, biosurfactants of biological origin may be used in addition to or instead of the surfactants mentioned above. Examples of biosurfactants are sophorose lipid, trehalose lipid or lipopeptides of the type known as metabolism products or membrane constituents of a number of microorganism strains. In this connection, the following additional consideration applies to the system according to the invention. The presence of biosurfactants can be guaranteed not only by the composition of the nutrient concentrate in initial steps of the remediation process. The in situ formation of metabolism products of biosurfactant character is also promoted by the nutrient mixtures during the microbiological degradation of the hydrocarbon compounds. In the same way as the phosphoric acid esters mentioned above, these biosurfactants act as dispersants and emulsifiers and thus accelerate the degradation of oil.

Sorbitan esters, for example sorbitan monostearate or sorbitan monooleate, may be used instead of or in addition to the nonionic surfactants mentioned above. Ethoxylated sorbitan esters may also be used, although they are less recommended.

The surfactant compounds mentioned above are present in the nutrient concentrates according to the invention in quantities of, typically, 0.5 to 5% by weight. In general, quantities of up to about 1% by weight of surfactant are sufficient to initiate and promote the intended impulse stimulation of microorganism growth. Thus, the surfactants based on alkyl glycoside compounds need only be used in quantities of around 0.5 to 1% by weight, based on the mixture as a whole, for effectively improving microorganism growth.

Nutrient concentrates of the type described in the foregoing are storable products which may initially be mixed with several times the quantity of water for application to solid and/or liquid surfaces. For example, the nutrient concentrate may be mixed with 5 to 50 times the quantity by weight of water, quantities of around 15 to 30 parts by weight of water to 1 part by weight of nutrient concentrate being preferred mixing ranges. The product may then be applied to the surfaces to be treated in this water-mixed form. The nutrient concentrate is incorporated in the contaminated soil sample in quantities of, preferably, 5 to 200 mg per g of pollution.

Particular advantages of the nutrient mixture according to the invention include, for example, its complete degradability, the fact that the nutrient mixtures according to the invention do not contain any ecologically harmful and/or unsafe chemicals and, at the same time, are comparatively inexpensive mixtures which may be applied quickly and easily, even over large areas. The growth and the effectiveness of the microflora present, for example, in oil-polluted soils is greatly promoted by this mixture of nutrients, selected oleophilic and hydrophilic carriers and emulsifiers. The use of limited quantities of emulsifiers from the outset increases the bioavailability of the, for example, oil-containing pollution. The attack of the microorganisms on the pollution is thus facilitated and its degradation accelerated.

In many cases, however, untreated oil-polluted soils and/or waters contain only small quantities of oil-degrading microorganisms. The result of this is that the natural microbial degradation of the pollution proceeds too slowly, particularly in the initial phase. In cases such as these, the teaching according to the invention provides for the use of microorganism concentrates adapted to the pollution in conjunction with the nutrient concentrates, at least at the beginning of the remediation process. To this end, the invention uses in particular non-pathogenic, harmless bacterial populations which have preferably been isolated from the environment and enriched in a separate preliminary stage. This inoculation of the soiled areas supports the microflora naturally present during the degradation of the hydrocarbon compounds. The degradation rate, for example the oil degradation rate, is thus significantly improved, particularly in the critical initial phase. In addition to the starter cultures, the natural nuclei mass together within a few days of the application of the auxiliaries initially applied and continue the degradation process. To guarantee broad application, it can be of advantage to use microorganism strains resistant to salt water as the starter cultures so that oil pollution, for example, can even be effectively treated at sea and on beaches.

In one important embodiment of the invention, the nutrient combinations are used together with microorganism concentrates which have been obtained by separate cultivation of natural strains isolated from hydrocarbon-contaminated localities of natural origin. It may be preferable in this regard to use concentrates of corresponding microorganism strains which in turn form biosurfactants as metabolism products. Without any claim to completeness, some possible starter cultures are listed in the following, although they are generally not used as isolated strains, but rather in the form of a mixture of a number of strains: *Pseudomonas oleovorans* DSM 1045; *Pseudomonas putida* DSM 548 and DSM 50208; *Acinetobacter calcoaceticus* DSM 590; *Nocardia paraffineus* ACC 21198; *Arthrobacter paraffineus* ATCC 15591.

The nutrient mixtures used in accordance with the invention and the microorganism cultures optionally used in conjunction with them may be used quite generally for the remediation of soils, fresh water and/or salt water and hence for the elimination and/or accelerated degradation of pollution based on hydrocarbon compounds on land and/or water. The application of considerable relevance in this regard today is the elimination of unwanted oil pollution, particularly crude oil pollution, and the elimination of corresponding old pollution from, typically, confined terrestrial areas. However, the teaching according to the invention may also be applied in a completely different manner. Thus, oil-polluted working equipment, for example pipes or large vessels up to and including tankers can be effectively decontaminated by bioremediation. Information on the particular technology to be used can be found in the relevant prior-art literature, see for example Al W. Bourquin "Bioremediation of Hazardous Waste" in "Biofuture", September 1990, 24 to 35.

In one particularly important embodiment, the invention relates to the use of the described nutrient mixtures, more particularly in combination with microorganism concentrates capable of degrading hydrocarbons, for the disposal of oil-wetted cuttings from geological land-supported or offshore drilling, for example from the development of valuable geological occurrences. The following circumstances prevail in this regard: in the development of, for example, crude oil and/or natural gas, borehole servicing fluids based on a continuous oil phase, which flow freely under normal conditions, are widely used at the present time. Characteristic examples of such fluids are drilling fluids and drilling muds of the w/o type based thereon. Other examples include so-called spotting fluids, spacers, auxiliary fluids for workover and stimulation and for fracturing.

In practice, borehole servicing fluids based on a continuous oil phase have hitherto been formed almost exclusively by mineral oil fractions. This entails considerable environmental pollution, for example if drilling muds enter the environment directly or through drilled rock. In the absence of additional auxiliary measures, mineral oils are not readily degradable and, anaerobically, are virtually non-degradable and may therefore be regarded as long-term pollution.

In recent years, some proposals have been put forward with a view to solving these problems. Thus, proposals for replacing the mineral oil fractions by ecologically safe, readily degradable oil phases are disclosed in a relatively large number of applications. Various types of replacement of replacement oils are mentioned and may even be used in the form of mixtures with one another. The replacement oils in question are based on selected oleophilic carboxylic acid esters, oleophilic diesters of carbonic acid, at least substantially water-insoluble oleophilic alcohols which flow freely under working conditions and correspond ethers. Summary reference is made in this regard to earlier applications DE 38 42 659, 38 42 703, 39 07 391, 39 07 392, 39 03 785, 39 03 784, 39 11 238, 39 11 299 and 40 18 228.

The teaching according to the invention for stimulating the microbial degradation of hydrocarbon-based components and, more particularly, corresponding oils may be used with particular advantage for the rapid elimination of oil pollution or residues, for example on the drill cuttings accumulating where oil-based systems such as these are used in practice. Hitherto, oil-wetted cuttings, for example from land-supported drilling, have always been transported to special waste disposal sites. It is known that the space available for this purpose is now limited. Accordingly, comparatively complicated surfactant-based washing processes have been proposed for the cleaning and, hence, easier disposal of such drilling residues. The teaching according to the invention provides for the accelerated microbial degradation of oil residues through the use of the nutrient concentrates, optionally in conjunction with starter cultures of suitable microorganisms. For example, the teaching according to the invention provides for the rapid elimination of oil-based drilling muds which are discharged from the borehole together with the drilled rock and which cannot be separated from the cuttings by conventional separation techniques, for example sieving. By partial recycling of the microorganism population developed during such treatment, the cuttings can be better prepared for disposal as waste.

In practice, the nutrient concentrates mentioned at the beginning are diluted with water, for example in a ratio of 1:20. If necessary, the starter culture of selected microorganisms, which is also used in accordance with the invention, may then be mixed in. The components should be mixed immediately before the ready-to-use mixture is applied to guarantee maximum effectiveness of the products. The ready-to-use mixtures may be applied over small or even large areas, for example by spraying. It may be useful to repeat the application at weekly intervals.

The replenishment of the nutrient concentrate may readily be monitored. Thus, where urea is used as the N-source, both the concentration of urea ions and the concentration of ammonium ions in the sample to be treated may be determined at the beginning of the treatment. The formation of ammonium ions indicates the metabolic activity of the microorganisms during their consumption of urea. Accordingly, the replenishment of the nutrients can be determined through the ammonium ion content, i.e. when urea has been consumed, more may optionally be added.

EXAMPLES

A nutrient concentrate was prepared from: Glycerophospholipid (enzymatically hydrolyzed lecithin, trade name: Lipotin® NE, a product of Lucas Meyer) 20% by weight Urea 20% by weight Alkyl polyglycoside (C chain length: $C_8$ to $C_{16}$, D.P.: approx. 1.4), 2% by weight and Water ad 100% by weight. The remediation of contaminated sand was simulated under the following conditions:

Test data for simulation of the industrially applied "Biobeet" remediation technique

| | |
|---|---|
| Substrate: | 2 kg sand |
| Pollution: | crude oil, 7,000 ppm |
| Incubation temperature: | 16° C. |
| Observation period: | 42 days |
| Treatment interval: | 0.4 g nutrient concentrate/kg sand every 10 days |
| Pollutant analysis method: | DIN 38409 H18 |

Result

| Incubation time (days) | Residual oil without treatment (%) | Residual oil after nutrient treatment (%) |
|---|---|---|
| 0 | 100 | 100 |
| 14 | 68 | 36 |
| 29 | 64 | 33 |
| 35 | 54 | 27 |
| 42 | 52 | 20 |
| Number of "degradation specialists" after 20 days | <10% | >70% |

The pollutant analysis method according to DIN 38409 H18 comprises determining the specific spectral absorption of hydrocarbon mixtures by infrared spectroscopy in an organic solvent extract. The number of "degradation specialists", i.e. the microorganisms capable of degrading the contamination, was determined by initially determining the total number of growing microorganisms or microorganisms capable of growth and then determining the number of degradation specialists from the result obtained by transferring the cultures to a nutrient plate containing hexadecane as sole C-source.

Behavior under marine conditions:

Test data for simulation of "beach remediation"

| | |
|---|---|
| Substrate: | 1 kg sea land, adjustment of ground moisture with seawater |
| Pollution: | 20,000 ppm old crude oil with no volatile constituents |
| Incubation temperature: | 15° C. |
| Observation period: | 42 days |
| Treatment interval: | 0.4 g nutrient concentrate/kg sand every 10 days |
| Pollutant analysis method: | gas chromatography |

Result

| Incubation time (days) | Residual oil without treatment (%) | Residual oil fractions after nutrient treatment (%) | | |
|---|---|---|---|---|
| | | C17 | C18 | C20 |
| 0 | 100 | 100 | 100 | 100 |
| 7 | 98 | 90 | 93 | 86 |
| 14 | 98 | 76 | 87 | 72 |
| 30 | 99 | 58 | 68 | 58 |
| 42 | 98 | 45 | 54 | 41 |

Result:

The nutrient concentrate activates the degradation potential of marine flora.

We claim:

1. A nutrient concentrate for promoting the growth and effectiveness of hydrocarbon-consuming microorganisms for their use in the biological degradation of organic components comprising A) at least one ester of phosphoric acid as an emulsifier and as a source of phosphorus; and B) from about 10 to about 40% by weight of urea as a source of nitrogen.

2. The nutrient concentrate of claim 1 wherein component A is present in from about 10 to about 40% by weight.

3. The nutrient concentrate of claim 2 which further contains from about 0.5 to about 5% by weight of at least one biocompatible surfactant other than a glycerol ester.

4. The nutrient concentrate of claim 1 wherein component A is present in from about 20 to about 30% by weight, and component B is present in from about 15 to about 30% by weight.

5. The nutrient concentrate of claim 4 which further contains from about 0.5 to about 5% by weight of at least one nonionic surfactant other than a glycerol ester.

6. The nutrient concentrate of claim 1 which further contains at least one biocompatible surfactant other than a glycerol ester.

7. The nutrient concentrate of claim 6 wherein the at least one surfactant is at least one nonionic surfactant.

8. The nutrient concentrate of claim 7 wherein the at least one nonionic surfactant is at least one of a $C_8$–$C_{24}$ alkyl glycoside, a partial sugar ester of $C_8$–$C_{24}$ monocarboxylic acids, a sorbitan ester, and a biosurfactant of biological origin.

9. The nutrient concentrate of claim 1 wherein component A is at least one of a phospholipid, an alkyl phosphate and an alkylether phosphate.

10. The nutrient concentrate of claim 1 wherein component A comprises a glycerophospholipid or an enzymatically hydrolyzed glycerophospholipid.

11. The nutrient concentrate of claim 1 diluted with from about 5 to about 50 times its quantity by weight of water.

12. A process for cleaning hydrocarbon-contaminated equipment, pipes and transporting vessels comprising applying thereto the diluted concentrate of claim 11 and a concentrate of microorganisms capable of degrading hydrocarbon compounds.

13. A process for the remediation of polluted soil or water comprising applying to the polluted soil or water the diluted concentrate of claim 11.

14. The process of claim 13 wherein the polluted soil or water is polluted with hydrocarbon compounds.

15. The process of claim 13 wherein the process is used for the biological disposal of invert drilling muds based on at least one of oleophilic carboxylic acid esters, oleophilic carbonic acid esters, oleophilic ethers, or oleophilic alcohols.

16. The process of claim 13 wherein at least one concentrate of microorganisms which are capable of degrading hydrocarbon compounds is also added to the polluted soil or water.

17. The process of claim 16 wherein the microorganisms were isolated from hydrocarbon-containing soil.

18. The process of claim 16 wherein the microorganisms form biosurfactants as metabolic products.

19. The nutrient concentrate of claim 1 wherein the dilution is with from about 15 to about 30 times its quantity by weight of water.

20. A process for the remediation of polluted soil or water comprising applying to the polluted soil or water the diluted concentrate of claim 19.

* * * * *